(12) United States Patent
Epstein et al.

(10) Patent No.: US 7,938,799 B2
(45) Date of Patent: May 10, 2011

(54) MEDICAL DEVICE FOR VESSEL COMPATIBILITY DURING HIGH PRESSURE INFUSION

(75) Inventors: Samuel J. Epstein, Watertown, MA (US); Toby Freyman, Waltham, MA (US); Chad G. Harris, Albertville, MN (US); Timothy J. Mickley, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 429 days.

(21) Appl. No.: 11/780,885

(22) Filed: Jul. 20, 2007

(65) Prior Publication Data
US 2008/0039786 A1  Feb. 14, 2008

Related U.S. Application Data

(60) Provisional application No. 60/836,656, filed on Aug. 10, 2006.

(51) Int. Cl.
*A61M 31/00* (2006.01)
*A61M 37/00* (2006.01)
(52) U.S. Cl. .................................. 604/103.03
(58) Field of Classification Search ............... 604/103.3
See application file for complete search history.

(56) References Cited

U.S. PATENT DOCUMENTS

| 5,273,052 A | 12/1993 | Kraus et al. |
| 5,403,274 A | 4/1995 | Cannon |
| 5,472,418 A | 12/1995 | Palestrant |
| 6,761,732 B2 * | 7/2004 | Burkett et al. ............... 623/1.11 |
| 2003/0158519 A1 | 8/2003 | Epstein et al. |
| 2003/0195527 A1 | 10/2003 | Helmus |

FOREIGN PATENT DOCUMENTS

| EP | 0533511 | 3/1993 |
| EP | 0820729 | 1/1998 |
| EP | 820729 A1 * | 1/1998 |

OTHER PUBLICATIONS

Partial International Search Report in PCT/US2007/017250, dated Dec. 18, 2007.
International Search Report and Written Opinion in PCT/US2007/017250, dated Jan. 29, 2008.

\* cited by examiner

*Primary Examiner* — Nicholas D Lucchesi
*Assistant Examiner* — Pritesh Patel
(74) *Attorney, Agent, or Firm* — Vidas, Arrett & Steinkraus (57) ABSTRACT

The invention provides devices that can be used to deliver a therapeutic agent to a treatment site within the vessel of a patient at increased pressure, while limiting the contact with and pressure placed on the vessel walls. Devices according to the invention include an expandable structure arranged around and on a tube having a lumen. The expandable structure may include a sealing ring that makes contact with the interior surface of a vessel to prevent or decrease fluid flow during delivery of a therapeutic agent. This allows delivery of a therapeutic agent with decreased risk of injury to the treatment site. The invention also provides for large lumen diameters, preventing shearing stress on therapeutic agents such as cell slurries.

22 Claims, 10 Drawing Sheets

MEDICAL DEVICE FOR VESSEL COMPATIBILITY DURING HIGH PRESSURE INFUSION

CROSS-REFERENCE

This application is related to application number U.S. 60/836,656 filed on Aug. 10, 2006, in the U.S. and claims priority to this application, which is incorporated herein by reference in it's entirety.

TECHNICAL FIELD

The present invention relates to the delivery of a therapeutic agent or other material to a treatment site.

BACKGROUND

Delivery of therapeutic agents to the interior of vessels is a growing field of interest. For example, adverse remodeling of the myocardium and associated long-term damage may be reduced or prevented by delivering mesenchymal stem cells after stent reperfusion following a myocardial infarction. This and other treatments are performed by positioning a standard angioplasty balloon near the treatment site. A balloon may be placed, for example, at the site of previous stenting. The balloon is inflated at or near the desired treatment site, and inflated to a pressure sufficient to seal the vessel and prevent blood flow. The guide-wire lumen of the balloon is then used to deliver a therapeutic agent.

Methods utilizing standard angioplasty and similar balloons and balloon catheters may be undesirable for several reasons. In general, the devices are neither designed for nor approved for such use. There is thus some uncertainty in the safety and effectiveness of such procedures. For example, the guide-wire lumens typically used with such balloons are relatively small, often about 0.015" or less. Some therapeutic agents, such as slurries of mesenchymal stem cells or other cells, may be relatively viscous and heterogeneous suspensions. When forced through the narrow guide-wire lumen, the lumen may become clogged. Forcing cell slurries through the narrow lumen may also result in high shear forces on the cells, rendering them inactive. Additionally, during occlusion of the vessel, the balloons can exert high radial pressure on the vessel. This pressure can result in trauma or damage to the vessel, causing well-known complications such as restenosis.

Stents are often utilized in place of or in conjunction with balloons in order to avoid restenosis and other similar conditions. As discussed above, use of a standard balloon catheter may be undesirable for delivery of desired or necessary therapeutic agents to a treatment site, such as a previously-positioned stent. However, treatments utilizing a bolus injection of therapeutic agent delivered at high pressure may still be desirable or necessary.

SUMMARY OF THE INVENTION

The invention provides devices that can be used to deliver a therapeutic agent to a treatment site within the vessel of a patient at increased pressure, while limiting the contact with and pressure placed on the vessel walls. Hence a bolus of therapeutic agent may be delivered with decreased risk of trauma or damage to the treatment site. Additionally, the invention provides for large lumen diameters, decreasing the risk of damage to the therapeutic agent being delivered due to shear stresses.

A device is provided that comprises a tube having a lumen and an expandable structure capable of sealing or obstructing fluid flow through the vessel near the treatment site. When the device is positioned at an intended treatment site, the expandable structure may be expanded by an operator of the device. The structure may be expanded to a size and with sufficient pressure to obstruct or occlude the flow of blood within the vessel. In certain embodiments, when the expandable structure is expanded, only a relatively small portion of the expandable structure will contact the vessel wall. For example, in certain embodiments the structure may contact the vessel along a length of about 1 mm or less. A bolus of therapeutic agent may be delivered under high pressure, via the lumen, and the expandable structure serves to substantially prevent backflow of the therapeutic agent.

It is believed that some therapeutic agents may be more effective if delivered under at least approximately physiologic pressure. For example, achieving physiologic pressure in the coronary vasculature may result in higher cell engraftment when the therapeutic agent being delivered includes a cell slurry. The expandable structure may substantially prevent backflow of the therapeutic agent, by providing sufficient pressure against the vessel wall to prevent collapse of the structure by the therapeutic agent being injected.

To accommodate high-pressure delivery, and also to prevent problems such as clogging of the lumen by therapeutic agents such as cell slurries, the invention may incorporate lumens of large diameter. The lumen may be, for example, at least about 0.5 mm in diameter.

In some embodiments, a sheath may be placed around the expandable structure to protect the expandable structure during insertion and positioning of the device within a vessel. For example, the expandable structure may be collapsed and the sheath positioned over and around the expandable structure. When the device is positioned at an intended delivery site, an operator of the device may retract the sheath or push the expandable structure out of the sheath. In such an embodiment, the expandable structure may be self-expanding such that removal of the sheath allows the expandable structure to spring open or self-expand. After a therapeutic agent has been delivered, the sheath may be repositioned over the structure to allow the device to be removed from the vessel.

DETAILED DESCRIPTION

Devices according to the invention comprise a tube having a lumen and an expandable structure capable of obstructing or occluding a vessel near a desired treatment site. When such a device is positioned at an intended treatment site, the expandable structure may be expanded by an operator of the device. While expanded, generally only a relatively small portion of the expandable structure will contact the vessel wall. In certain embodiments, the structure contacts the vessel along a length of about 1 mm or less. It is believed that such reduction in contact with the vessel may reduce the likelihood of injury to tissue or reinjury to damaged tissue. Once there is substantially no blood flow in the region of the treatment site, a bolus of therapeutic agent may be delivered via the lumen. The expandable structure can prevent or minimize backflow of the therapeutic agent. After delivery of the therapeutic agent, the expandable structure may then be contracted, and the device withdrawn from the treatment site. Lumens used with the invention may be relatively large, allowing for therapeutic agents such as cell slurries to be used without clogging the lumen or causing undesirable strain on the cells. In certain embodiments, the lumen may be at least about 0.5 mm in diameter. Different lumen sizes may also be used for specific applications.

The invention will now be described with respect to various specific illustrations and examples. Unless stated otherwise, the device may be positioned within a vessel of a patient such that blood flow is from the proximal end of the device to the distal end (right to left in the figures). It will be understood that this convention is for illustration purposes only, and one of skill in the art could adapt the devices described to be used in the alternate direction, i.e., such that blood flow is from the distal end to the proximal end. Components described with respect to a previous illustration have been labeled with the same identifiers for convenience.

Figure 1:
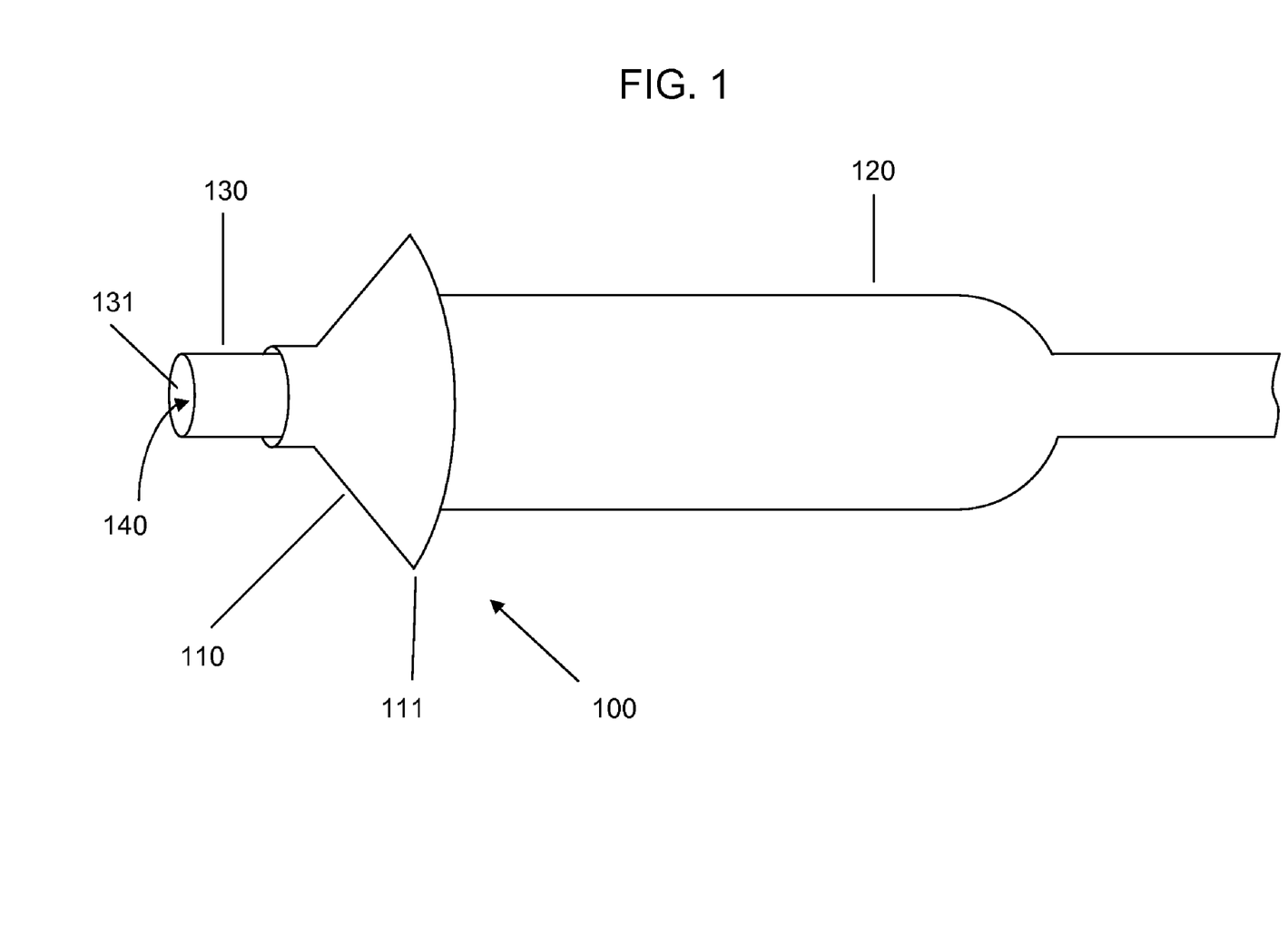
FIG. 1 shows an enlarged side view of an expandable structure according to an embodiment of the invention that includes a skirt.

An embodiment of a device according to the invention is shown in FIG. 1. An expandable structure 100 is disposed at one end or along the length of a delivery mechanism, such as a catheter or guide wire (not shown). An operator of the device may position the device at a desired treatment site within a vessel and expand the structure to occlude blood flow within the vessel.

In this embodiment, the expandable structure 100 is expanded by an inflatable balloon 120. The balloon 120 is disposed on a tube 130 having a lumen 140. Different diameter lumens may be utilized based on the specific application. For example, to deliver a therapeutic agent comprising a slurry of mesenchymal stem cells, a diameter of at least about 0.5 mm may be preferred. The balloon 120 may be similar to, or formed from, a standard angioplasty or similar balloon, or the materials and size used may be selected for a specific application. In this embodiment, the expandable structure 100 is in the form of an expandable skirt 110 having a sealing ring 111 disposed on the outside of the inflatable balloon. To prevent damage such as restenosis to the treatment site, the balloon 120 has an expanded diameter less than the diameter of the vessel, such that it does not fully contact the vessel wall when fully inflated as shown in FIG. 1. The skirt 110 therefore provides the only sealing contact with the vessel, reducing the risk of additional injury.

When the balloon is inflated, the skirt 110 expands as shown to touch the inner wall of the vessel. Pressure may be applied to the skirt 110 via inflation of the balloon 120, causing the sealing ring 111 to contact the inner wall of the vessel. The sealing ring may contact the vessel across a length (i.e., the distance between the proximal-most contact point and the distal-most contact point) when the structure is expanded. In certain embodiments, the sealing ring may contact the vessel wall across a length of not more than about 1 mm. The sealing ring 111 may be formed of the same material as the skirt 110, i.e., it may be the edge of the skirt 110, or it may be formed of a different material.

When the expandable structure 100 has been expanded via inflation of the balloon 120, a therapeutic agent may be ejected from the distal end 131 of the lumen 140. The skirt 110 may remain in place during and after delivery of the therapeutic agent to prevent backflow of the therapeutic agent. After delivery of the therapeutic agent, the expandable structure 100 may be contracted and the device withdrawn from the vessel. For example, the skirt 110 may contract upon deflation of the balloon 120 to simplify insertion, positioning, and withdrawal of the device.

Figure 2:
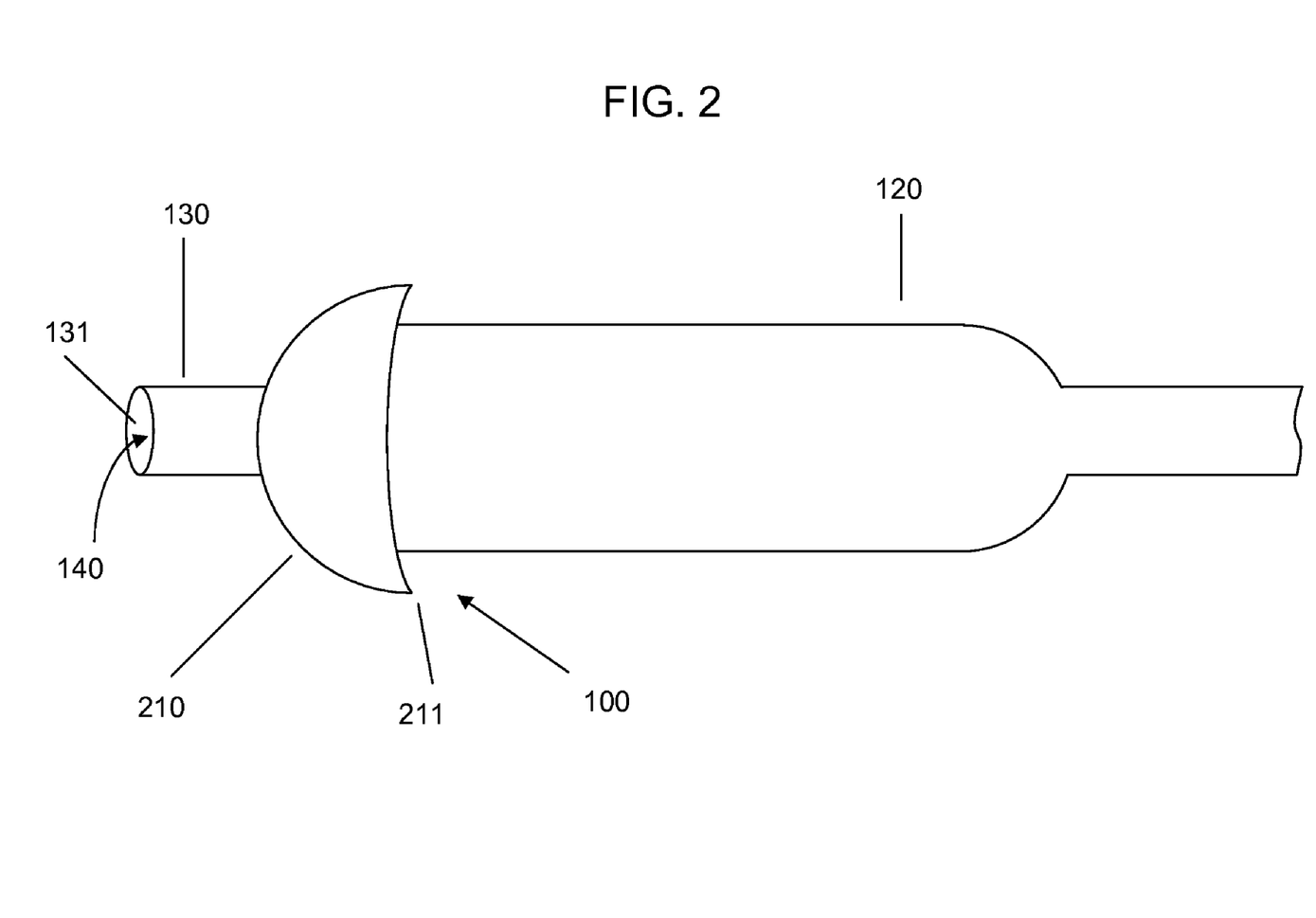
FIG. 2 shows an enlarged side view of an expandable structure according to an embodiment of the invention that includes a skirt.

A similar embodiment is shown in FIG. 2. As with the device illustrated in FIG. 1, the device shown in FIG. 2 includes an expandable structure 100 that an operator of the device may expand to obstruct or occlude the flow of blood and/or therapeutic agent within the vessel. An expandable skirt 210 may be expanded by pressure from the inflated balloon 120 such that the edge of the skirt 211 contacts the inner surface of the vessel. As previously described, the skirt 210 may provide sufficient pressure against the inner surface of the vessel to prevent the flow of blood and/or therapeutic agent within the vessel.

Figure 3A:
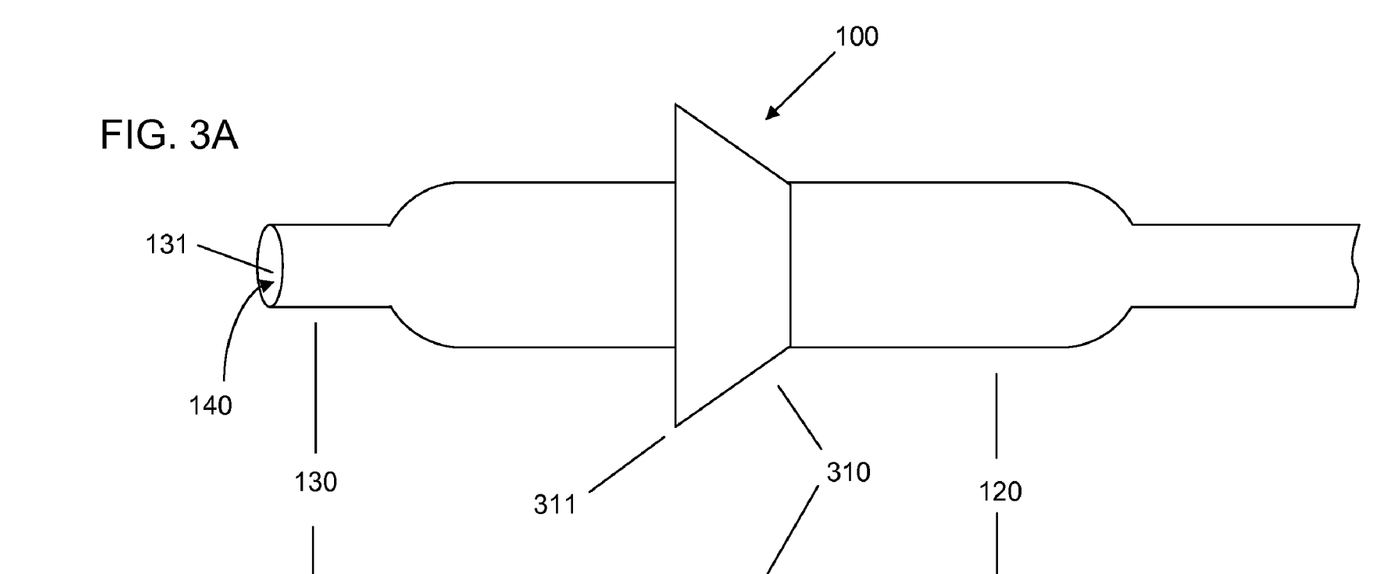
FIG. 3 shows an enlarged side view of an expandable structure according to an embodiment of the invention that includes a skirt.
Figure 3B:
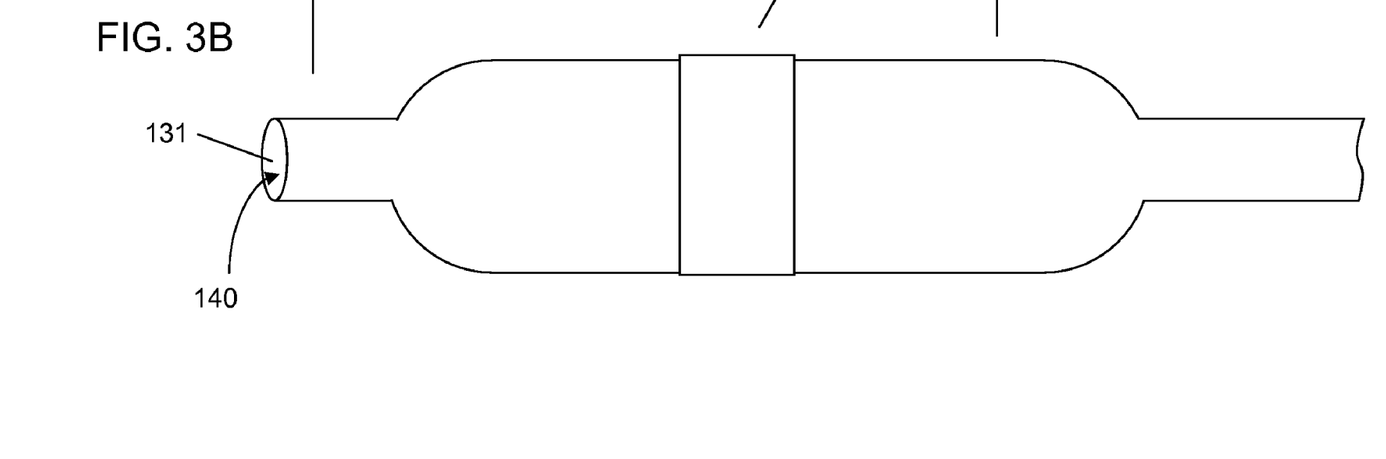

For some applications, it may be preferable to prevent blood flow only while the therapeutic agent is being delivered, or only after a certain amount of therapeutic agent has been delivered. One such configuration is illustrated in FIG. 3. After the device is placed at a desired treatment site, an operator of the device may inflate the balloon 120 as previously described with respect to FIGS. 1-2. An expandable skirt 310 is disposed along the length of the balloon. The skirt 310 acts as a pressure valve when the device is disposed within the vessel of a patient. That is, it may remain collapsed until forced open by pressure from one side. In such an embodiment, the skirt remains closed as shown in FIG. 3B. When a sufficient pressure develops on the distal side of the skirt, the skirt is forced open as shown in FIG. 3A. For example, the skirt may be forced open by pressure resulting from ejection of a therapeutic agent from the distal end 131 of the lumen 140. In such a configuration, the skirt remains collapsed until therapeutic agent is delivered. As therapeutic agent is ejected from the lumen, pressure on the distal side of the skirt 310 increases, causing the skirt to expand. When the skirt expands such that the sealing ring 311 contacts the interior surface of the vessel, blood flow within the vessel may be substantially prevented. Such occlusion allows the therapeutic agent to be delivered to the intended treatment site without being diluted or removed by the flow of blood, but does not require occlusion of the vessel for longer than the time required to deliver the therapeutic agent. In another configuration, the device may be positioned such that fluid pressure from blood flow causes the skirt 310 to expand, substantially preventing flow past the skirt. When the balloon is deflated the skirt 310 may then collapse, allowing the device to be withdrawn from the vessel.

Figure 4:
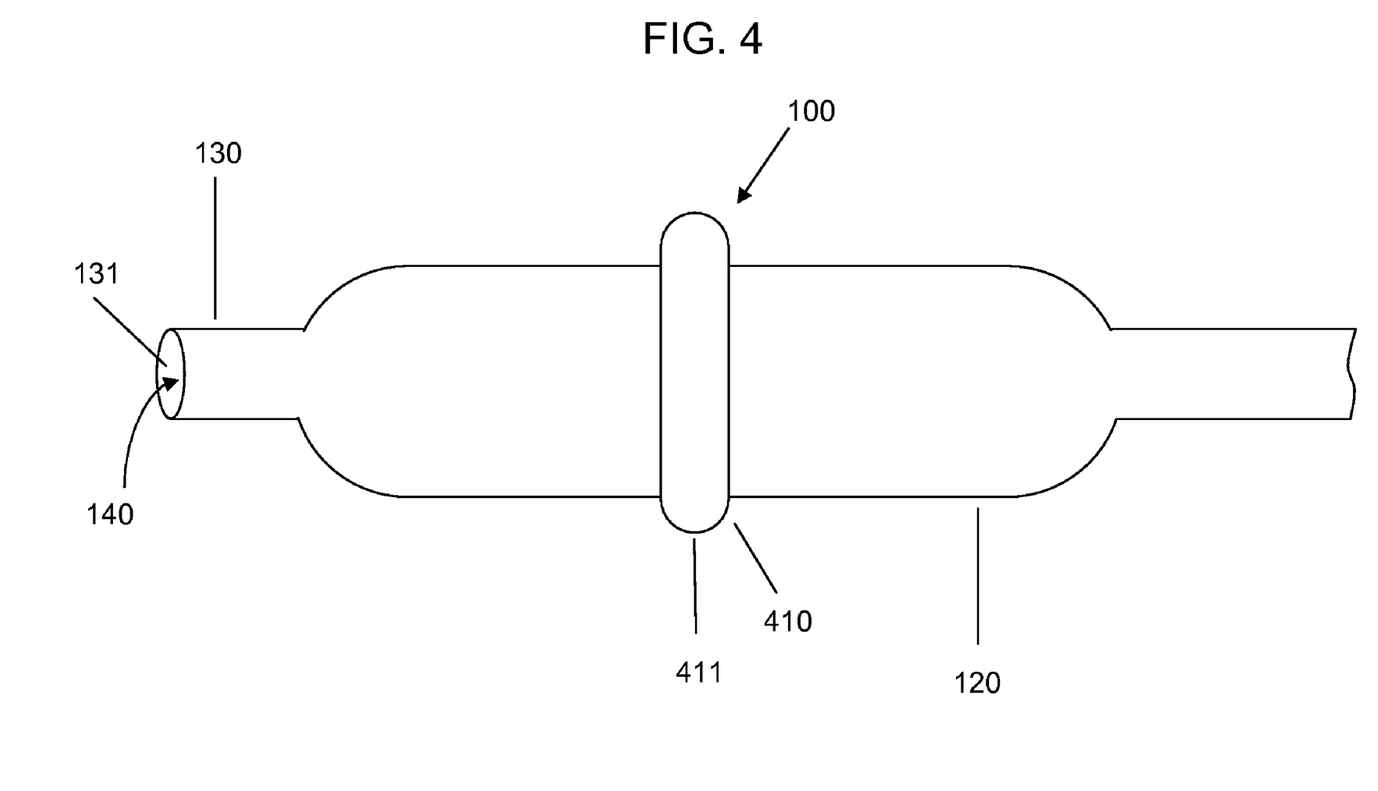
FIG. 4 shows an enlarged side view of an expandable structure according to an embodiment of the invention that includes a deformable band.

In some applications, it may be desirable to utilize a configuration that not only limits the area of the vessel with which the device comes into contact, but also the amount of pressure exerted by the device. Such a device is illustrated in FIG. 4. A balloon 120 is disposed near the distal end of a catheter or other delivery mechanism. When the balloon is inflated, a deformable band 410 may expand outward from the lumen until the edge 411 of the band contacts the inner surface of the vessel. The band 410 may be made of a soft or rubbery material, and may include a coating such as hydrogel or other soft coating to reduce potential trauma or damage to the interior surface of the vessel while still preventing fluid flow. The specific hardness and flexibility of the band may be selected based on the specific application. If soft or easily-damaged materials are required, the expandable structure 100 may include a packaging (not shown) to protect the band prior to deployment at a treatment site.

Figure 5A:
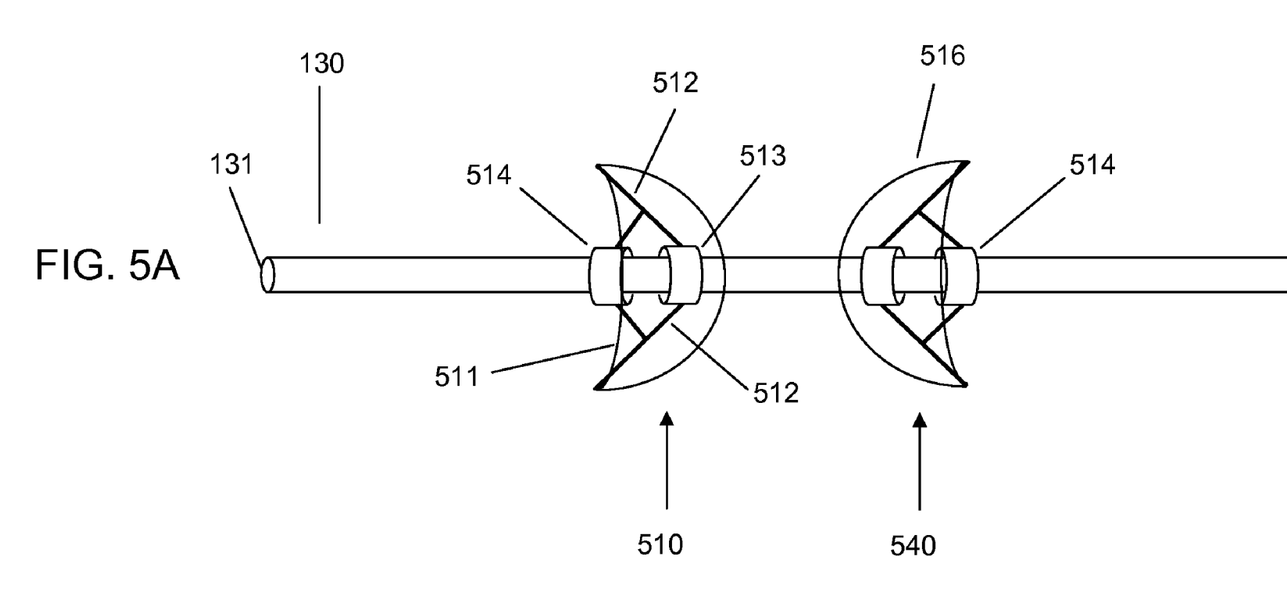
FIG. 5 shows enlarged side and cut-away views of expandable structures according to embodiments of the invention that include struts and flexible membranes.
Figure 5B:
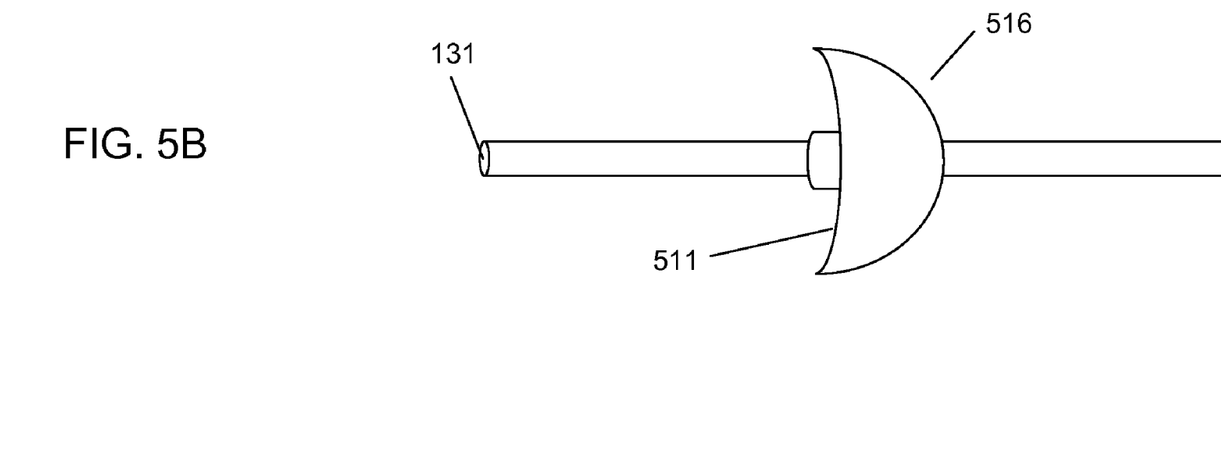

Some embodiments do not utilize a balloon as part of the expandable structure; these configurations may be used, for example, in locations presenting difficulty in maneuvering or deploying a balloon-type device. FIG. 5 illustrates one such embodiment. FIG. 5A shows a side cut away view exposing interior components. FIG. 5B shows a side view with interior components not shown. An expandable structure 510 comprises multiple struts 512 and a flexible membrane 516. A moveable cuff 514 is disposed on the tube 130, and is connected flexibly or by hinged connections to multiple struts 512. The struts are also flexibly connected to a point on the tube, which may be a second cuff 513. An operator may move the cuff 514 towards the cuff 513, causing the struts 512 to open. When the struts are opened to a sufficient distance, the ends of the struts may contact the inner surface of a vessel. The flexible membrane 516 connected to and spanning the struts 512 may prevent fluid flow within the vessel when the struts are open. A sealing ring 511 formed by or disposed on the edge of the membrane may be made of the same material as the flexible membrane, or it may be made of a different material. For example, the sealing ring 511 may be made of a shape memory material that causes the sealing ring to be roughly circular in shape. The edge of the flexible membrane may form the sealing ring when the expandable structure is open. When the structure 510 is open, it may occlude the vessel to prevent backflow of therapeutic agent ejected from the distal end 131 of the lumen 140.

In some embodiments, a second expandable structure 540 similar to the first expandable structure 510 may be disposed on the proximal side of the first structure 510, such that opening the struts causes a second membrane and/or sealing ring to be deployed in the proximal direction. When the structure is expanded, the second structure 540 may prevent blood flow within the vessel in the distal direction, similar to the operation of the first structure 510 with respect to the therapeutic agent. Use of two expandable structures may be desirable to prevent each structure from being collapsed by fluid pressure against the flexible membrane. For example, fluid pressure against the expandable structure 510 in the distal direction may cause the membrane to collapse or be less effective in preventing fluid flow in the proximal direction.

Figure 6A:
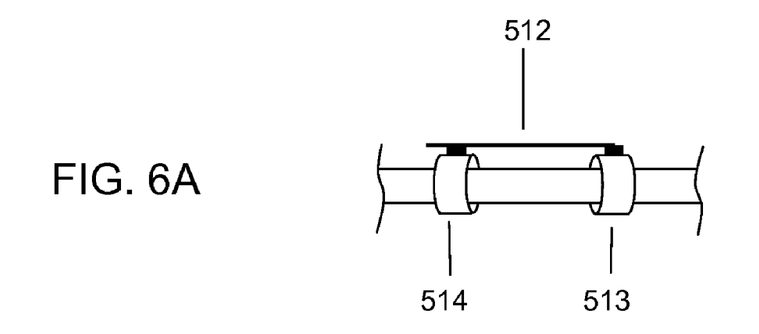
FIG. 6 shows enlarged views of parts of the expandable structures shown in FIG. 5.
Figure 6B:
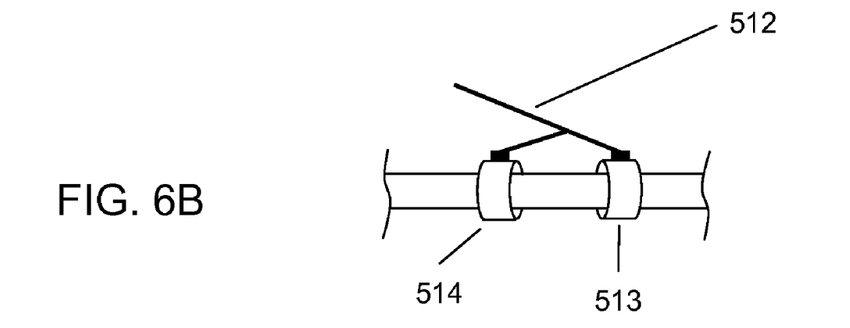
Figure 6C:
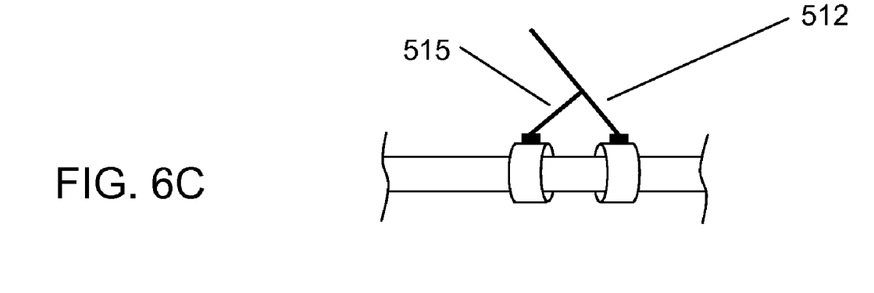

An expanded view of the struts, cuffs, and opening mechanism is shown in FIG. 6. For clarity, only a single strut is shown. It will be understood that any number of struts may be used. Prior to expansion of the structures 510, 540, the struts 512 and cuffs 513, 514 are in an initial position as shown in FIG. 6A. When the device is positioned at an intended treatment site, an operator of the device may move the moveable cuff 514 toward the stationary cuff 513. Although the moveable cuff is shown as being closer to the distal end of the lumen, it will be understood that the moveable cuff may be on either side of the stationary cuff, and that struts may be attached to the tube in configurations other than those shown. For example, in the second expandable structure 540 shown in FIG. 5, the moveable cuff is disposed on the proximal side of the stationary cuff. When the moveable cuff 514 is moved toward the stationary cuff, the struts 512 are forced open. FIG. 6B shows the moveable cuff in an intermediate position. The device may include various additional struts, wires, or other mechanisms to cause the struts to open. For example, FIG. 6 shows auxiliary struts 515 connecting the struts 512 to the moveable cuff 514. When the struts reach a desired opening, as shown in FIG. 6C, an operator of the device may leave the moveable cuff 514 in the position corresponding to that arrangement of struts.

As previously described with reference to FIG. 5, some embodiments of the invention may include multiple expandable structures 510, 540. The invention may allow an operator to expand each structure individually, or it may allow for the two structures to be expanded simultaneously. For example, the moveable cuffs 514 may be connected, such that moving one in a proximal direction causes the other to move in a distal direction. After delivery of a therapeutic agent, the structure or structures may be contracted by moving the moveable cuffs 514 in the opposite direction from that used to expand the structures.

Figure 7A:
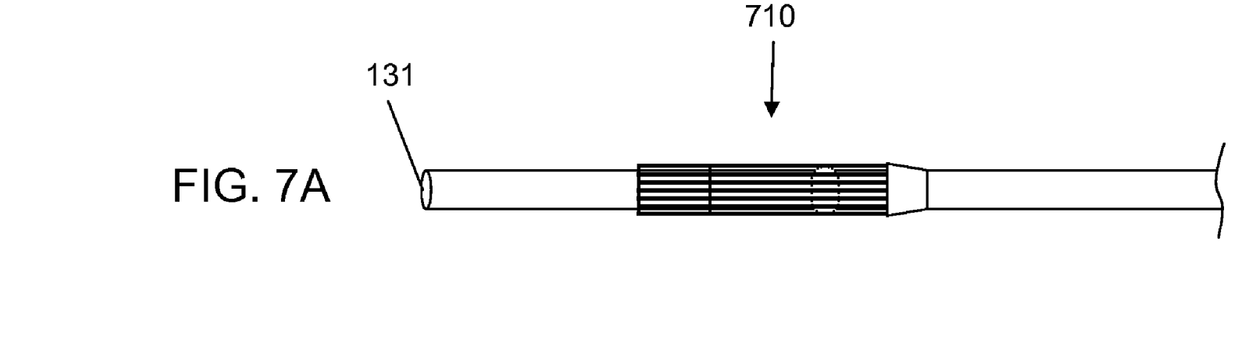
FIG. 7 shows enlarged side views of an expandable structure according to an embodiment of the invention that includes moveable struts.
Figure 7B:
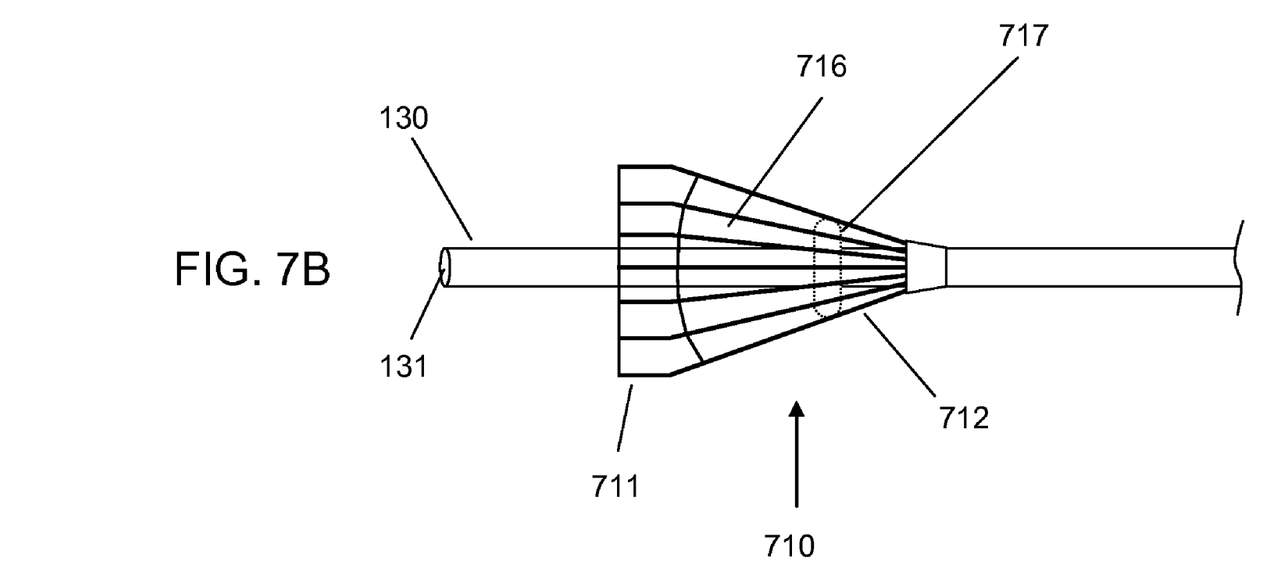

Another embodiment of the invention is shown in FIG. 7. As previously described, the device may be positioned within the vessel of a patient, expanded, and later contracted after delivery of a therapeutic agent. The expandable structure 710 shown in FIG. 7 comprises multiple struts 712, which when opened within a vessel form a sealing ring 711 on the interior surface of the vessel. A flexible membrane 716 may be disposed between and connected to the struts 712. An inflatable balloon 717 disposed around the tube 130 and between the tube and the struts may be inflated by an operator of the device to open the struts 712. The struts 712 may be flexible, so that the length of the sealing ring 711 is determined by the amount of pressure placed on the struts by the inflated balloon 717. The struts may also be rigid or semi-rigid, such that the length of the sealing ring is pre-determined. As shown in FIG. 7A, the expandable structure may be collapsed to aid in positioning the device.

Figure 8A:
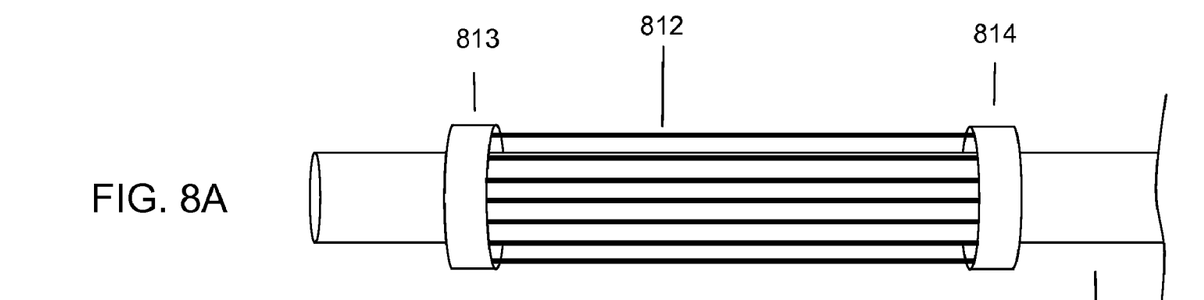
FIG. 8 shows enlarged side views of an expandable structure according to an embodiment of the invention that includes connected struts.
Figure 8B:
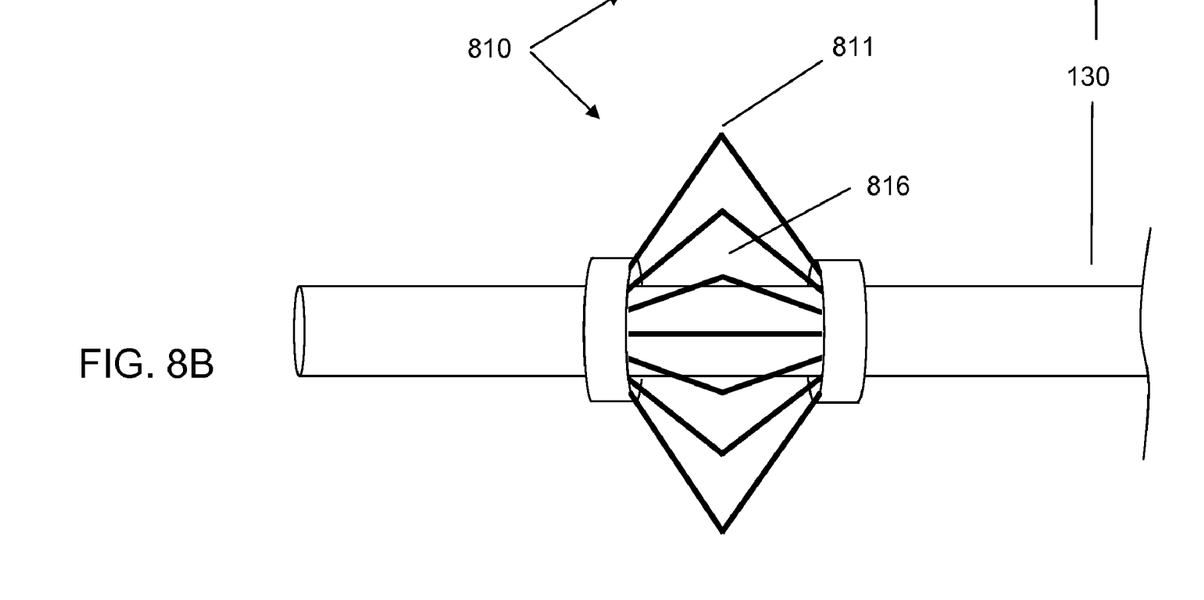

FIG. 8 shows another embodiment of the invention. The expandable structure 810 comprises a plurality of flexible struts 812 and a flexible membrane 816. Two cuffs 813, 814 may be connected to the flexible struts 812. Similarly, each cuff may be flexibly connected to a number of struts, which are then connected at the opposite ends to a second set of struts flexibly connected to the other cuff. When one or both of the cuffs 813, 814 are moved along the tube so that they are closer together, the struts 812 move outward from the lumen as shown in FIG. 8B. One cuff may be fixed, e.g., the distal cuff 813 may be moved toward the proximal cuff 814 by an operator, or both cuffs may be moveable. When placed at a treatment site within a vessel, the struts may be expanded by moving one or both of the cuffs. The struts may then contact the inner surface of the vessel, with the outermost points of the cuffs 811 defining a sealing ring to prevent the flow of fluid within the vessel. The flexible membrane 816, similar to that described with respect to FIGS. 5-7, is disposed between the struts 812. When the struts are expanded, the membrane may form a sealing ring against the surface of the vessel to prevent fluid flow. The device may include a mechanism allowing one or both of the cuffs to be locked in place after the struts are expanded, to prevent the struts from collapsing due to fluid pressure. After delivery of a therapeutic agent, the cuff or cuffs can be returned to their original position, causing the struts and flexible membrane to contract.

Figure 9A:
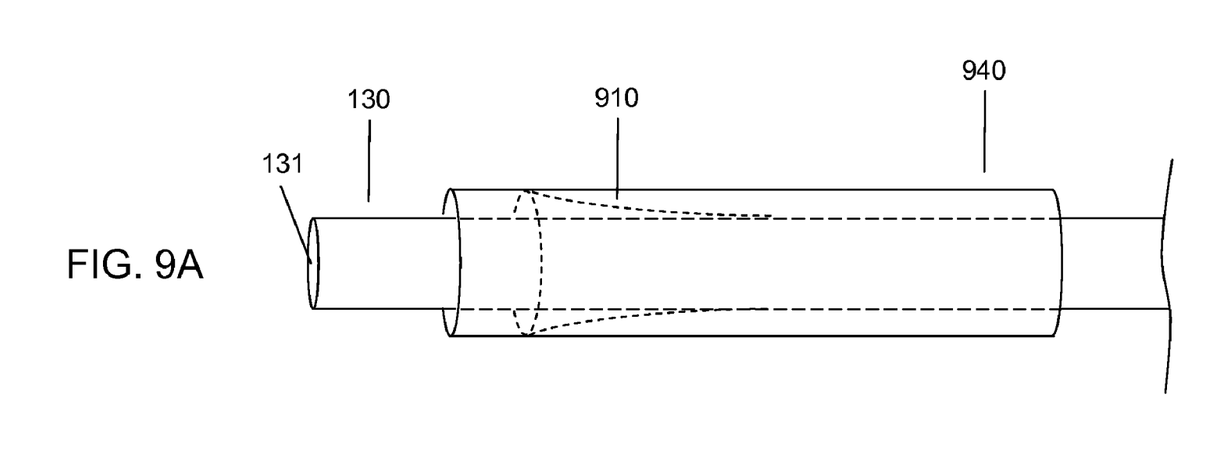
FIG. 9 shows enlarged side and cut away views an of an expandable structure according to an embodiment of the invention that includes an expandable cone.
Figure 9B:
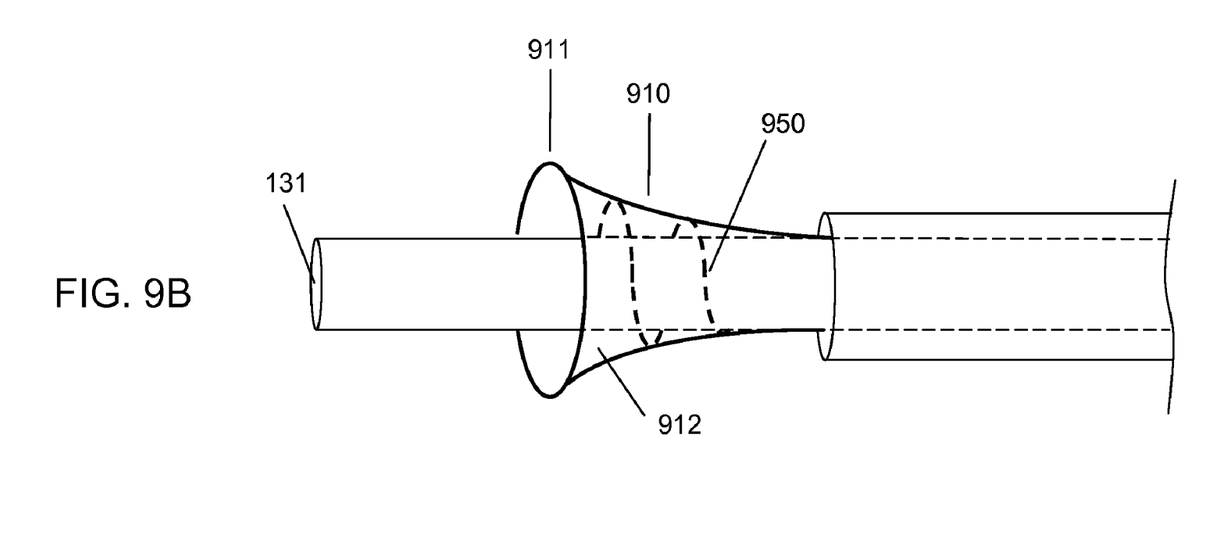

In another embodiment of the invention, the expandable structure comprises a flexible cone. FIG. 9 shows one such embodiment. A flexible cone 910 is disposed near the distal end of the lumen 130. The cone may be formed of any suitable material. In certain embodiments, the cone comprises a shape memory material such as Nitinol. Similarly, the cone may be made of a frame of shape memory material, with a flexible membrane 912 attached across it. The membrane may be made of any suitable material. In some embodiments, an interior spring 950 may be disposed within the cone or within the flexible membrane. When the sheath is retracted or the cone extended out of the sheath, the spring 950 and/or shape memory material may cause the cone 910 to expand.

Prior to delivery of a therapeutic agent through the lumen, the cone may be compressed within a sheath 940 that is moveable along the axis of the lumen. When the sheath 940 is retracted toward the proximal end of the lumen by an operator, the cone 910 may expand. The distal end of the cone may form a sealing ring 911 that makes contact with the interior surface of the vessel in which the device is deployed. The cone 910 and sealing ring 911 may prevent flow of fluid within the vessel, including distal flow of blood and/or proximal flow of the therapeutic agent ejected from the distal end 131 of the lumen.

Figure 10A:
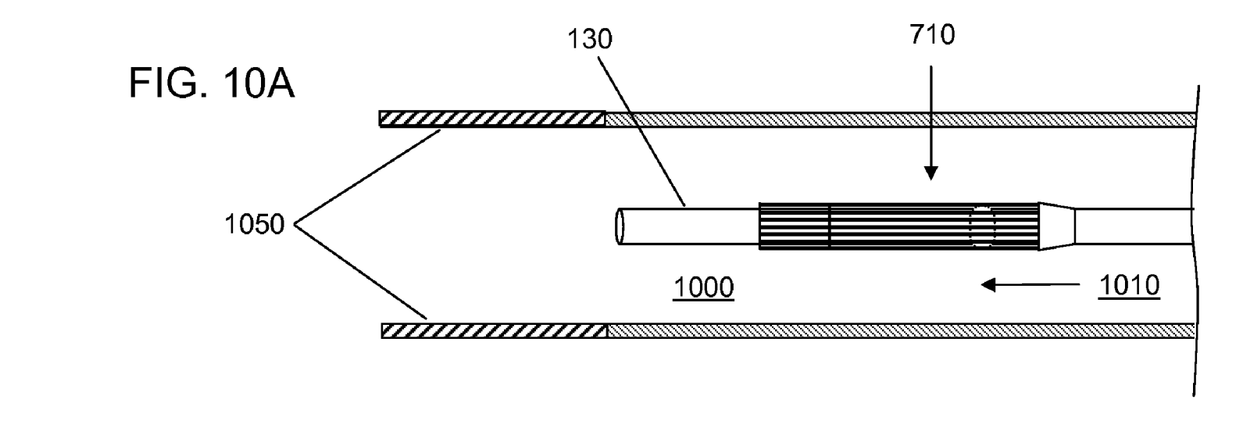
FIG. 10 shows an enlarged side cut away view of a device according to an embodiment of the invention positioned within the vessel of a patient.
Figure 10B:
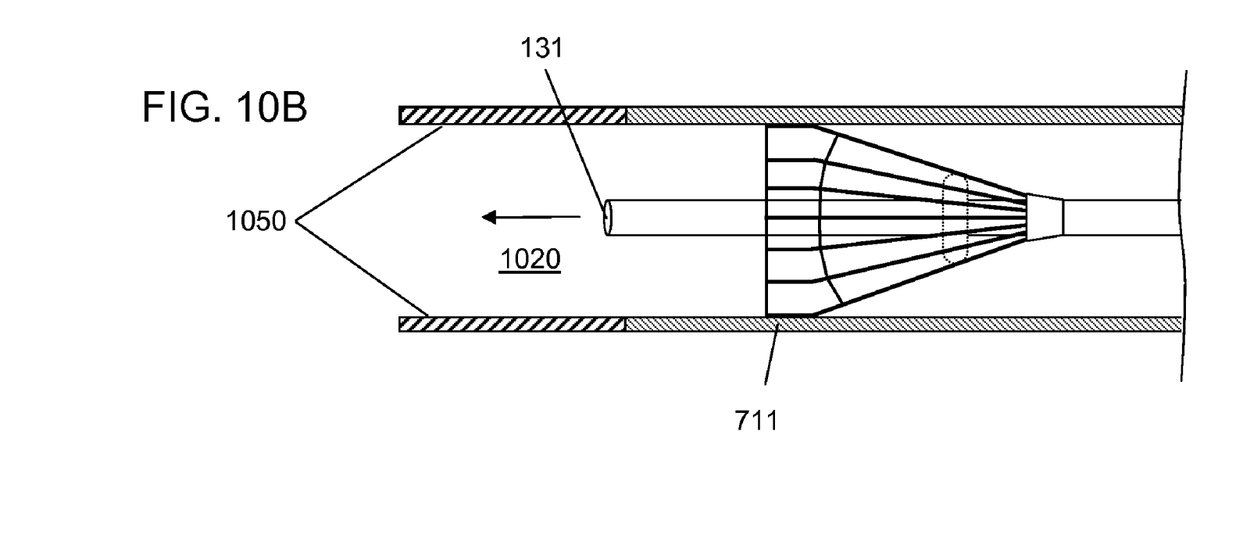

FIG. 10 shows an example of a device according to the invention positioned within the vessel of a patient. The device described with reference to FIG. 7 is shown as an example; it will be understood that each embodiment of the invention, including those described with reference to FIGS. 1-6 and 8-9, may be operated in a similar manner. The tube 130 is placed at an intended delivery site 1050, as shown in FIG. 10A. An expandable structure 710 is disposed on the outside of the tube. The direction of blood flow 1010 is shown by the arrow in FIG. 10A. Prior to delivery of a therapeutic agent, an operator of the device may expand the expandable structure 710 to form a sealing ring 711 around the interior surface of the vessel, as shown in FIG. 10B. In preferred embodiments, the region along which the expandable structure 710 contacts the interior vessel surface 711 is not more than about 1 mm. A therapeutic agent may be ejected from the distal end 131 of the lumen. Flow of the therapeutic agent 1020 is shown by the arrow in FIG. 10B. The therapeutic agent contacts the intended delivery site 1050 under pressure. In preferred embodiments, the device allows delivery of therapeutic agent under at least about physiologic pressure.

It will be understood that various components discussed with reference to specific figures may be used in any of the embodiments discussed. For example, the sheath 950 described with reference to FIG. 9 may be used with any of the other embodiments described, such as with the expandable frame described with respect to FIGS. 5-7. Other embodiments may include components and materials from various specific arrangements described herein.

It will be understood that the drawings described herein are provided for illustration purposes and intended to show specific aspects of the invention. The drawings therefore may not be to scale. For example, the lumens shown may be larger or smaller relative to the expandable structures than is shown in the figures.

As used herein and as will be understood by one of skill in the art, the "proximal" end of a device or portion of a device refers to the end closest to the operator of the device. Similarly, the "distal" end of a device or portion of a device refers to the end farthest from the operator of the device.

The term "therapeutic agent" as used throughout includes one or more "therapeutic drugs" or "genetic material." The term "therapeutic agent" used herein includes pharmaceutically active compounds, nucleic acids with and without carrier vectors such as lipids, compacting agents (such as histones), virus (such as adenovirus, adenoassociated virus, retrovirus, lentivirus and a-virus), polymers, hyaluronic acid, proteins, cells and the like, with or without targeting sequences. The therapeutics administered in accordance with the invention includes the therapeutic agent(s) and solutions thereof.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as nonsteroidal anti-inflammatory agents and chelating agents such as ethylenediaminetetraacetic acid, O,O'-bis(2-aminoethyl) ethyleneglycol-N,N,N',N'-tetraacetic acid and mixtures thereof, antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; bAR kinase (bARKct) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; extracellular matrices; decellularized extracellular matrices; matrix proteins; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factor ÿ and ÿ, platelet-derived endothelial growth factor, platelet-derived growth factor, tumor necrosis factor ÿ, hepatocyte growth factor, and insulin like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogeneic), or genetically engineered. Non-limiting examples of cells include side population (SP) cells, lineage negative (Lin-) cells including Lin-CD34−, Lin-CD34+, Lin-cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device, into a polymeric, controlled-release microsphere, or applied onto a polymeric coating on a medical device. The polymers of the polymeric coatings may be biodegradable or non-biodegradable. Non-limiting examples of suitable non-biodegradable polymers include polystrene; polyisobutylene copolymers, styrene-isobutylene block copolymers such as styrene-isobutylene-styrene tri-block copolymers (SIBS) and other block copolymers such as styrene-ethylene/butylene-styrene (SEBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by various methods including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

The examples described and illustrated herein are merely illustrative, as numerous other embodiments may be implemented without departing from the spirit and scope of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A medical device comprising: a tube having a proximal end, a distal end, an outer surface between the proximal end and the distal end, and a lumen; an inflatable balloon disposed on the outer surface of the tube between the proximal end and the distal end and axially aligned with the tube, the balloon having an outer surface, and the balloon inflatable from a first position to a second position; and an expandable structure axially aligned with the tube and in physical contact with the outer surface of the inflatable balloon, the expandable structure comprising: a plurality of struts; a membrane disposed between and connected to the first plurality of struts; wherein the struts and the membrane form a sealing ring at a distal region of the expandable structure; wherein the expandable structure is expandable by the balloon from a first position to a second position; wherein the expandable structure is expanded to the second position when the inflatable balloon is inflated to the second position; wherein the diameter of the expandable structure in the second position is substantially greater than the diameter of the inflatable balloon in the second position; and
wherein, when the expandable structure is in the second position, the sealing ring of the expandable structure contacts the inner surface of the vessel with sufficient pressure to substantially prevent passage of fluid through the vessel.

2. The medical device of claim 1 wherein the expandable structure comprises a skirt.

3. The medical device of claim 1 wherein the expandable structure is disposed at an end of the inflatable balloon.

4. The medical device of claim 1 wherein the expandable structure is a deformable band.

5. The medical device of claim 4 wherein the expandable structure comprises a soft material.

6. The medical device of claim 1 wherein the expandable structure has a soft coating.

7. The medical device of claim 6 wherein the soft coating is hydrogel.

8. The medical device of claim 1 wherein the lumen is at least about 0.5 mm in diameter.

9. The medical device of claim 1 wherein, when the device is disposed within a vessel of a patient and the expandable structure is in the second position, the sealing ring of the expandable structure contacts the interior wall of the vessel across a length of not more than about 1 mm.

10. A medical device, comprising: a tube having a proximal end, a distal end, and a lumen; a first cuff disposed around and on the tube; and an expandable structure comprising: a first plurality of struts, each of the first plurality of struts connected to the first cuff; and a first membrane disposed between and connected to the first plurality of struts; and
an inflatable balloon axially aligned with the lumen, the balloon inflatable from a first position to a second position, wherein: the inflatable balloon is disposed on one side of the first cuff;
each of the first plurality of struts is connected at one end to the first cuff and extends over the inflatable balloon; and
the end of each of the first plurality of struts not connected to the first cuff is moved radially outward from the lumen when the inflatable balloon is inflated to the second position, thereby causing the first membrane to expand;
wherein, when the device is disposed within a vessel of a patient and the inflatable balloon is in the second position, the struts and membrane of the expandable structure forming a sealing ring at a distal end of the expandable structure that contacts the inner surface of the vessel;
and wherein the first plurality of struts exert sufficient pressure against the inner surface of the vessel that the membrane substantially prevents passage of fluid.

11. The medical device of claim 10, wherein the sealing ring contacts an inner surface of the vessel across a length of not more than about 1 mm.

12. The medical device of claim 10, wherein the lumen is at least about 0.5 mm in diameter.

13. The medical device of claim 10, wherein the first cuff is moveable along the longitudinal axis of the lumen from a first position to a second position.

14. The medical device of claim 13, wherein one end of each of the first plurality of struts is moved radially outward from the lumen when the first cuff is moved to the second position.

15. The medical device of claim 14, wherein, when the device is disposed within a vessel within the body of a patient and the first cuff is in the second position, the expandable structure contacts the inner surface of the vessel.

16. The medical device of claim 15, wherein the first plurality of struts exert sufficient pressure against the inner surface of the vessel that the membrane substantially prevents passage of fluid.

17. The medical device of claim 10, further comprising:
a second cuff disposed around and on the tube; and a second expandable structure comprising:

a second plurality of struts, each of the second plurality of struts connected to the second cuff; and a second membrane connected to the second plurality of struts.

18. The medical device of claim 17, wherein: the first cuff is moveable along the longitudinal axis of the lumen from a first position to a second position; the second cuff is moveable along the longitudinal axis of the lumen from a first position to a second position; one end of each of the first plurality of struts is moved radially outward from the lumen when the first cuff is moved to the second position; and one end of each of the second plurality of struts is moved radially outward from the lumen when the second cuff is moved to the second position.

19. A medical device comprising: means for delivering a bolus of therapeutic agent at or above physiologic pressure within a vessel of a patient; and an expandable structure for substantially preventing flow of fluid within the vessel, the expandable structure comprising: a plurality of struts; a membrane disposed between and connected to the first plurality of struts; and a sealing ring at a distal end of the expandable structure; and an inflatable balloon having an outer surface in physical contact with the expandable structure; and wherein the expandable structure is expandable by the inflatable balloon from a first position to a second position;

wherein, when the device is disposed within the vessel and the expandable structure is in the second position, the expandable structure substantially prevents back-flow of the therapeutic agent after delivery of the therapeutic agent; and the expandable structure substantially prevents flow of blood within the vessel.

20. The medical device of claim 19, wherein the expandable structure can be expanded or contracted by an operator of the device.

21. The medical device of claim 19, wherein, when the device is disposed within a vessel of a patient, the sealing ring of the expandable structure contacts the inner surface of the vessel along a length of not more than about 1 mm.

22. The medical device of claim 19, wherein the means for delivering a bolus of therapeutic agent comprises a lumen of at least about 0.5 mm in diameter.

* * * * *